United States Patent
Kaib

(10) Patent No.: US 10,993,693 B2
(45) Date of Patent: *May 4, 2021

(54) THERAPEUTIC DEVICE INCLUDING ACOUSTIC SENSOR

(71) Applicant: ZOLL MEDICAL CORPORATION, Chelmsford, MA (US)

(72) Inventor: Thomas E. Kaib, Irwin, PA (US)

(73) Assignee: ZOLL MEDICAL CORPORATION, Chelmsford, MA (US)

(*) Notice: Subject to any disclaimer, the term of this patent is extended or adjusted under 35 U.S.C. 154(b) by 31 days.

This patent is subject to a terminal disclaimer.

(21) Appl. No.: 16/382,491

(22) Filed: Apr. 12, 2019

(65) Prior Publication Data

US 2019/0231301 A1    Aug. 1, 2019

Related U.S. Application Data

(63) Continuation of application No. 15/918,617, filed on Mar. 12, 2018, now Pat. No. 10,307,133, which is a continuation of application No. 14/314,799, filed on Jun. 25, 2014, now Pat. No. 9,955,938.

(60) Provisional application No. 61/839,693, filed on Jun. 26, 2013.

(51) Int. Cl.
| | |
|---|---|
| *A61B 7/04* | (2006.01) |
| *G10L 25/48* | (2013.01) |
| *A61B 5/00* | (2006.01) |
| *A61B 5/282* | (2021.01) |
| *A61N 1/04* | (2006.01) |

(52) U.S. Cl.
CPC .............. *A61B 7/04* (2013.01); *A61B 5/282* (2021.01); *A61B 5/6833* (2013.01); *G10L 25/48* (2013.01); *A61B 2562/028* (2013.01); *A61B 2562/0219* (2013.01); *A61N 1/0484* (2013.01)

(58) Field of Classification Search
USPC .................................................. 600/300–301
See application file for complete search history.

(56) References Cited

U.S. PATENT DOCUMENTS

| | | | |
|---|---|---|---|
| 5,078,134 | A | 1/1992 | Heilman et al. |
| 7,010,342 | B2 | 3/2006 | Galen et al. |
| 7,065,397 | B2 | 6/2006 | Galen et al. |
| 7,074,195 | B2 | 7/2006 | Nelson et al. |
| 7,096,060 | B2 | 8/2006 | Arand et al. |

(Continued)

OTHER PUBLICATIONS

International Search Report from corresponding PCT application PCT/US2014/044129, dated Nov. 4, 2014.

*Primary Examiner* — Nicole F Lavert
(74) *Attorney, Agent, or Firm* — Lando & Anastasi, LLP

(57) ABSTRACT

A therapeutic device comprises an ECG sensing electrode configured to be disposed on a torso of a subject, a therapy electrode to be disposed on the torso of the subject, the therapy electrode comprising a substrate and a conductive layer disposed on a lower surface of the substrate, and an acoustic sensor coupled to one of the ECG sensing electrode and the therapy electrode, the acoustic sensor being configured to acoustically couple to the torso of the subject and monitor heart sounds indicative of a state of health of a heart of the subject. The therapeutic device is configured to store data regarding the heart sounds monitored by the acoustic sensor and transmit the stored data to an external system for processing and analysis.

20 Claims, 7 Drawing Sheets

(56) References Cited

U.S. PATENT DOCUMENTS

| | | |
|---|---|---|
| 7,110,804 B2 | 9/2006 | Baumer et al. |
| 7,174,203 B2 | 2/2007 | Arand et al. |
| 7,302,290 B2 | 11/2007 | Bauer |
| D566,847 S | 4/2008 | Baumer |
| 7,668,589 B2 | 2/2010 | Bauer |
| 8,105,241 B2 | 1/2012 | Nelson et al. |
| 8,185,190 B2 | 5/2012 | Bauer |
| 8,406,842 B2 | 3/2013 | Kaib et al. |
| 8,409,108 B2 | 4/2013 | Bauer et al. |
| 8,577,448 B2 | 11/2013 | Bauer et al. |
| 2006/0100535 A1 | 5/2006 | Bauer |
| 2006/0135876 A1 | 6/2006 | Andresen |
| 2006/0155202 A1 | 7/2006 | Arand et al. |
| 2006/0251269 A1 | 11/2006 | Bauer |
| 2007/0038137 A1 | 2/2007 | Arand et al. |
| 2007/0191725 A1 | 8/2007 | Nelson |
| 2008/0255465 A1 | 10/2008 | Nelson |
| 2009/0043218 A1 | 2/2009 | Warner et al. |
| 2009/0069857 A1 | 3/2009 | Bucher et al. |
| 2009/0138059 A1 | 5/2009 | Ouwerkerk |
| 2010/0298899 A1* | 11/2010 | Donnelly ........... A61N 1/37258 607/6 |
| 2011/0066041 A1 | 3/2011 | Pandia et al. |
| 2011/0279963 A1 | 11/2011 | Kumar et al. |
| 2012/0011382 A1 | 1/2012 | Volpe et al. |
| 2012/0150008 A1* | 6/2012 | Kaib ....................... A61B 5/04 600/372 |
| 2012/0303079 A1* | 11/2012 | Mahajan ............ A61N 1/36557 607/14 |
| 2012/0317024 A1* | 12/2012 | Rahman ................ G06Q 30/02 705/42 |

\* cited by examiner

THERAPEUTIC DEVICE INCLUDING ACOUSTIC SENSOR

RELATED APPLICATIONS

This Application claims priority under 35 U.S.C. § 120 as a continuation of U.S. patent application Ser. No. 15/918,617, titled "THERAPEUTIC DEVICE INCLUDING ACOUSTIC SENSOR," filed on Mar. 12, 2018, now U.S. Pat. No. 10,307,133, which in turn claims priority under 35 U.S.C. § 120 as a continuation of U.S. patent application Ser. No. 14/314,799, titled "THERAPEUTIC DEVICE INCLUDING ACOUSTIC SENSOR," filed on Jun. 25, 2014, now U.S. Pat. No. 9,955,938, which in turn claims priority under 35 U.S.C. § 119(e) to U.S. Provisional Application Ser. No. 61/839,693, titled "THERAPY ELECTRODE INCLUDING ACOUSTIC SENSOR," filed on Jun. 26, 2013. Each of these Applications is herein incorporated by reference in its entirety.

BACKGROUND

1. Technical Field

Aspects and embodiments of the present disclosure are directed to medical therapy systems, and more particularly, to electrode systems such as medical electrodes including one or more acoustic sensors and systems for analyzing heart sounds detected by the one or more acoustic sensors.

2. Discussion of Related Art

Cardiac arrest and other cardiac health ailments are a major cause of death worldwide. Various resuscitation efforts aim to maintain the body's circulatory and respiratory systems during cardiac arrest in an attempt to save the life of the victim. The sooner these resuscitation efforts begin, the better the victim's chances of survival. These efforts are expensive and have a limited success rate, and cardiac arrest, among other conditions, continues to claim the lives of victims.

To protect against cardiac arrest and other cardiac health ailments, some at-risk subjects may use a non-invasive bodily-attached ambulatory medical monitoring and treatment device, such as the LifeVest® wearable cardioverter defibrillator available from ZOLL LifeCor Corporation, a subsidiary of ZOLL Medical Corporation. To remain protected, the subject wears the device nearly continuously while going about their normal daily activities, while awake, and while asleep.

SUMMARY

In accordance with an aspect of the present disclosure, there is provided a therapeutic device comprising a layer configured to deliver a therapy to a subject and an acoustic sensor on the device and coupled to the layer. The acoustic sensor may comprise a three axis multiple-channel MEMS accelerometer. The acoustic sensor and associated electronics may be configured to provide an indication of whether the therapeutic device has been correctly oriented on a subject. The acoustic sensor may comprise a three-channel accelerometer.

In some embodiments, the therapeutic device comprises a therapy electrode comprising a conductive layer configured to deliver the therapy to the subject. The therapy electrode may be configured to selectively apply a defibrillation shock to the subject and/or to provide electrical pacing of a heart of the subject. The therapy electrode may be configured to monitor an ECG of the subject. In other embodiments, the therapy comprises a defibrillation pulse. In some embodiments, the therapy electrode further comprises an electrically conductive gel reservoir configured to release an electrically conductive gel onto a surface of the conductive layer. The acoustic sensor may be mechanically coupled to the layer, and it may be electrically coupled to the layer. The acoustic sensor may be acoustically coupled to the surface of the conductive layer through a cap housing the conductive gel reservoir. The acoustic sensor may be adhered to an internal surface of the cap. The acoustic sensor may be adhered to an upper wall of the cap. The acoustic sensor may be coupled to a system configured to record signals indicative of sounds produced by a heart of a patient. The therapeutic device may further comprise a connector or signal conductor electrically coupling the acoustic sensor to a circuit board coupled to the therapeutic device, the connector or signal conductor coupled to the therapeutic device with sufficient slack to provide for the therapy electrode to flex. In other embodiments, the slack may be provided by the extending connector along a multi-dimensional path.

In some embodiments, the therapeutic device includes an adhesive layer configured to adhere the device to the subject.

In some embodiments, the therapeutic device further comprises a controller configured to prompt the subject to provide a verbal response prior to delivery of a therapy, in some embodiments a defibrillation pulse, and to halt delivery of the therapy responsive to the voice of the subject being detected by the acoustic sensor. The controller may be configured to differentiate between the voice of the subject and a voice of a person other than the subject detected by the acoustic sensor. The controller may be configured to perform different actions responsive to detection of the voice of the subject by the acoustic sensor and detection of the voice of the person other than the subject by the acoustic sensor.

In accordance with another aspect of the present disclosure, there is provided an electrode assembly comprising a substrate, and an electrically conductive layer disposed on the substrate. The electrically conductive layer forms an electrode portion of the electrode assembly. The electrically conductive layer has a first surface configured to be placed adjacent a patient's skin. The electrode assembly further comprises an impedance reduction system configured to dispense an electrically conductive gel onto the first surface of the electrically conductive layer in response to an activation signal, and an acoustic sensor disposed on the electrode portion of the electrode assembly and acoustically coupled to the electrically conductive layer. The electrode assembly may further comprise at least one ECG sensing electrode configured to monitor an ECG of the patient.

The acoustic sensor may comprise a three axis multiple-channel MEMS accelerometer. The acoustic sensor may comprise a three-channel accelerometer. In some embodiments, a first channel of the three-channel accelerometer is configured to monitor sounds produced by a heart of the patient, a second channel of the three-channel accelerometer is configured to monitor a respiration of the patient, and a third channel of the three-channel accelerometer is configured to monitor movement of the patient.

In some embodiments, the acoustic sensor is configured to be electrically coupled to a system configured to record signals indicative of sounds produced by a heart of the patient. The system may be further configured to analyze the signals indicative of the sounds produced by the heart of the patient. The system may be further configured to warn the patient responsive to the sounds produced by the heart of the patient being indicative of an abnormal cardiac condition of the patient.

In some embodiments, the impedance reduction system includes a conductive gel reservoir configured to releasably store an amount of the electrically conductive gel to be dispensed onto the first surface of the electrically conductive layer in response to the activation signal. The acoustic sensor may be acoustically coupled to the electrically conductive layer through a cap enclosing the conductive gel reservoir. The acoustic sensor may be mechanically coupled to an internal wall of the cap. The acoustic sensor may be disposed on an upper internal wall of the cap.

In accordance with another aspect of the present disclosure, there is provided a method of monitoring physiological parameters of a subject. The method comprises monitoring heart sounds of the subject using an acoustic sensor physically coupled to a therapeutic device such as a therapy electrode or a defibrillation electrode and monitoring at least one additional parameter associated with a state of the subject using the acoustic sensor, the at least one additional parameter including one or more of a parameter associated with respiration of the subject, gastrointestinal sounds of the subject, snoring of the subject, and body movement of the subject.

In some embodiments, the at least one additional parameter further includes body position of the subject. The parameter associated with respiration of the subject may include one of sounds of respiration of the subject and movement of a chest of the subject. Monitoring at least one additional parameter associated with a state of the subject may comprise monitoring two or more additional parameters associated with a state of the subject.

In accordance with another aspect of the present disclosure, there is provided a method of monitoring physiological parameters of a subject. The method comprises providing a therapeutic device such as a therapy electrode or a defibrillation electrode having at least one acoustic sensor acoustically coupled to the therapeutic device, the at least one acoustic sensor being configured to monitor heart sounds of the subject, and to further monitor at least one additional physiological parameter of the subject, the at least one additional physiological parameter including one or more of a parameter associated with respiration of the subject, gastrointestinal sounds of the subject, snoring of the subject, and body movement of the subject.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
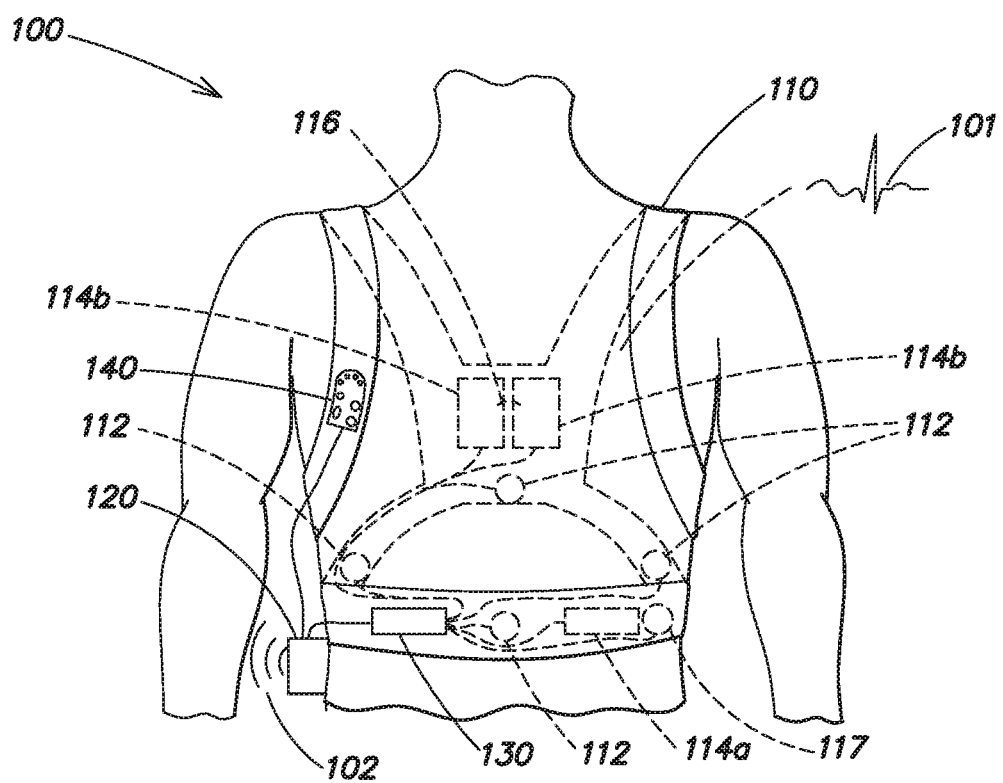
FIG. 1 illustrates a wearable medical device, such as a wearable defibrillator.

Aspects and embodiments of the present invention are not limited in application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

FIG. 1 illustrates a non-invasive bodily-attached ambulatory medical monitoring and treatment device 100 (also referred to herein as a wearable medical device), such as a LifeVest® wearable cardioverter defibrillator available from ZOLL Medical Corporation. As shown, the wearable medical device 100 includes a harness 110 having a pair of shoulder straps and a belt that is worn about the torso of a subject. The harness 110 is typically made from a material, such as cotton, which is breathable, and unlikely to cause skin irritation, even when worn for prolonged periods of time. In some embodiments, the wearable medical device 100 may include a plurality of ECG sensing electrodes 112 that are attached to the harness 110 at various positions about the subject's body and electrically coupled to a control unit 120 via a connection pod 130. The plurality of ECG sensing electrodes 112, which may be dry-sensing capacitance electrodes, are used by the control unit 120 to monitor the cardiac function of the subject and generally include a front/back pair of ECG sensing electrodes and a side/side pair of ECG sensing electrodes. Additional ECG sensing electrodes may be provided, and the plurality of ECG sensing electrodes 112 may be disposed at varying locations about the subject's body.

The wearable medical device 100 also includes a plurality of therapy electrodes 114a, 114b that are electrically coupled to the control unit 120 via the connection pod 130 and which are capable of delivering one or more therapeutic defibrillating shocks to the body of the subject, if it is determined that such treatment is warranted. In other embodiments, the therapy electrodes may provide other forms of therapy, such as electrical pacing of a subject's heart as needed or electric current to stimulate nerves as a part of Transcutaneous Electrical Nerve Stimulation (TENS) therapy. As shown, the plurality of therapy electrodes includes a first therapy electrode 114a that is disposed on the front of the subject's torso and a second therapy electrode 114b that is disposed on the back of the subject's torso. The second therapy electrode 114b includes a pair of therapy electrodes that are electrically coupled together and act as the second therapy electrode 114b. The use of two therapy electrodes 114a, 114b permits a biphasic shock to be delivered to the body of the subject, such that a first of the two therapy electrodes may deliver a first phase of the biphasic shock with the other therapy electrode acting as a return, and the other therapy electrode may deliver the second phase of the biphasic shock with the first therapy electrode acting as the return. In some embodiments, the belt of the harness 110 is positioned higher on the torso of a subject than is illustrated in FIG. 1 so that the plurality of ECG sensing electrodes 112 and the plurality of therapy electrodes 114a, 114b are generally disposed in a plane intersecting the subject's heart. In some embodiments, any one or more of the ECG sensing electrodes 112 and therapy electrodes 114a, 114b may include an adhesive layer, for example, an electrically conductive adhesive, to facilitate holding the electrodes in a proper position on the subject.

The connection pod 130 electrically couples the plurality of ECG sensing electrodes 112 and the plurality of therapy electrodes 114a, 114b to the control unit 120, and may include electronic circuitry. For example, in one implementation the connection pod 130 includes signal acquisition circuitry, such as a plurality of differential amplifiers to receive ECG signals from different ones of the plurality of ECG sensing electrodes 112 and to provide a differential ECG signal to the control unit 120 based on the difference therebetween. The connection pod 130 may also include other electronic circuitry, such as a motion sensor or accelerometer by which subject activity may be monitored.

In some embodiments, the therapy electrodes 114a, 114b may be multi-purpose electrodes. For example, under control of the control unit 120, the therapy electrodes 114a, 114b may deliver a defibrillation shock to a subject and may provide electrical pacing of a subject's heart or electrical current as a part of TENS therapy as needed.

As shown in FIG. 1, the wearable medical device 100 also includes a user interface pod 140 that is electrically coupled to the control unit 120. The user interface pod 140 may be attached to the subject's clothing or to the harness 110, for example, via a clip (not shown) that is attached to a portion of the interface pod 140. Alternatively, the user interface pod 140 may simply be held in a person's hand. In some embodiments, the user interface pod 140 may communicate wirelessly with the control unit 120, for example, using a Bluetooth™, Wireless USB, ZigBee, Wireless Ethernet, GSM, or other type of communication interface. The user interface pod 140 typically includes a number a number of buttons by which the subject, or a bystander may communicate with the control unit 120, and a speaker by which the control unit 120 may communicate with the subject or the bystander. For example, where the control unit 120 determines that the subject is experiencing cardiac arrhythmia, the control unit 120 may issue an audible alarm via a speaker (not shown) on the control unit 120 and/or the user interface pod 140 alerting the subject and any bystanders to the subject's medical condition. The control unit 120 may also instruct the subject to press and hold one or more buttons on the control unit 120 or on the user interface pod 140 to indicate that the subject is conscious, thereby instructing the control unit 120 to withhold the delivery of one or more therapeutic defibrillating shocks. If the subject does not respond, the device may presume that the subject is unconscious, and proceed with the treatment sequence, culminating in the delivery of one or more defibrillating shocks to the body of the subject. In some embodiments, the functionality of the user interface pod 140 may be integrated into the control unit 120.

The control unit 120 generally includes at least one processor, microprocessor, or controller, such as a processor commercially available from companies such as Texas Instruments, Intel, AMD, Sun, IBM, Motorola, Freescale and ARM Holdings. In one implementation, the at least one processor includes a power conserving processor arrangement that comprises a general purpose processor, such as an Intel® PXA270 processor and a special purpose processor, such as a Freescale™ DSP56311 Digital Signal Processor. Such a power conserving processor arrangement is described in co-owned U.S. Pat. No. 8,904,214, titled SYSTEM AND METHOD FOR CONSERVING POWER IN A MEDICAL DEVICE, which is incorporated by reference herein in its entirety. The at least one processor of the control unit 120 is configured to monitor the subject's medical condition, to perform medical data logging and storage, and to provide medical treatment to the subject in response to a detected medical condition, such as cardiac arrhythmia. The control unit 120 also includes a display (not shown), for example, a touch screen display (not shown), through which the subject may receive messages and interact with the wearable medical device. The wearable medical device 100 may include additional sensors 117, other than the ECG sensing electrodes 112, capable of monitoring the physiological condition or activity of the subject. For example, sensors capable of measuring blood pressure, heart rate, thoracic impedance, pulse oxygen level, respiration rate, heart sounds, and the activity level of the subject may also be provided.

It has been discovered that the analysis of the sounds 101 made by a subject's heart due to electro-mechanical activity of the heart may provide valuable information regarding the state of health of the subject's heart. This information may be used in conjunction with or in place of ECG data to provide, for example, an indication of possible problems with a subject's heart or of a potential impending cardiac event such as cardiac arrest. The analysis of the sounds of a subject's heart may also be monitored over longer periods of time, for example, days, weeks, or months, to identify whether the subject's cardiac condition is improving or worsening. Examples of systems and methods for analyzing the sounds from a subject's heart and the information such analysis may provide are described in U.S. Pat. Nos. 7,302,290, 7,668,589, and 8,409,108, each of which are incorporated herein by reference in their entireties.

Thus, in some embodiments, in addition to or in place of ECG sensing electrodes 112, the wearable medical device 100 may include one or more acoustic sensors or audio transducers 260 (shown in FIG. 3A) configured to detect sounds made by the subject's heart. The acoustic sensor(s) or audio transducer(s) 260 may be provided on or within one or more portions of the wearable medical device 100. The acoustic sensor(s) or audio transducer(s) 260 may be disposed within portions of the harness 110 or within or coupled to one of the ECG electrodes 112 or therapy electrodes 114a, 114b. The acoustic sensor(s) or audio transducer(s) 260 may be disposed on or within electrodes which are disposed on any of the front, rear, or side of a subject. The acoustic sensor(s) or audio transducer(s) 260 may be disposed within electrodes which are attached to the harness 110 and held against the skin of a subject wearing the wearable medical device 100 and/or disposed within adhesive electrodes which are adhered to the skin of the subject (see FIG. 4). The acoustic sensor(s) or audio transducer(s) 260 may be disposed within electrodes including multiple integrated components including, for example, ECG electrodes, therapy electrodes, and impedance reduction systems or may be included in an otherwise single function electrode.

In some embodiments it may be desirable to locate the acoustic sensor(s) or audio transducer(s) 260 proximate to or in contact with the skin of a subject so that heart sounds may be more easily detected than if the acoustic sensor(s) or audio transducer(s) 260 were spaced from the subject's body. It may be desirable that the acoustic sensor(s) or audio transducer(s) 260 are acoustically coupled to the subject's heart even if the acoustic sensor(s) or audio transducer(s) 260 are not in direct physical contact with the subject's skin. In some embodiments it may be desirable to locate the acoustic sensor(s) or audio transducer(s) 260 proximate to or in contact with the skin of a subject proximate the subject's heart, for example, proximate the left ventricle of the heart, so that the heart sounds are not attenuated by travel through a significant portion of the subject's body. In some embodiments, an electrode portion of a therapy electrode assembly in a wearable medical device 100 may be located above a subject's heart in contact with the subject's skin when the wearable medical device 100 is worn. Thus, in some embodiments, the acoustic sensor(s) or audio transducer(s) 260 may be disposed on or in the electrode portion of a therapy electrode assembly which is arranged to be located proximate the subject's heart, for example, proximate the left ventricle of the subject's heart.

The control unit 120 may include a memory unit to record data regarding the heart sounds. In some embodiments, recorded heart sound data may be stored on a removable memory card, for example, an SD card. A processor within the control unit may analyze the heart sounds for indications of potential problems with the subject's heart. Alternatively or additionally, the data regarding the heart sounds may be transmitted to an external system for processing and analysis. This transmission may occur through a wired connection to an external system or wirelessly, through, for example, Bluetooth™, Wi-Fi, or through a cellular network.

Feedback 102 may be provided to the subject through a display or speaker on, for example, the control unit 120 if the analysis of the subject's heart sounds 101 provides an indication of a problem with the subject's heart or of a potential for an impending cardiac event, for example, cardiac arrest. The results of the analysis of the subject's heart sounds may also be accessed through an external device, for example, a home computer through a web site or through a display of an external system to which the heart sound data may have been transmitted for analysis.

In healthy adults, there are two normal heart sounds, commonly referred to as S1 and S2. A third heart sound, commonly referred to as S3 (also called a protodiastolic gallop or ventricular gallop), may be indicative of a problem with a subject's heart when present. For example, in subjects over 40 years old, S3 has been associated with an abnormal diastolic filling pattern. The presence of S3 may signal cardiac problems like a failing left ventricle as in dilated congestive heart failure. A fourth heart sound, commonly referred to as S4 (also called a presystolic gallop or atrial gallop), is indicative of a problem with a subject's heart when present. For example, S4 is often associated with an increased left ventricular stiffness. Heart murmurs may also be present in some subjects and may indicate cardiac problems.

The acoustic sensor(s) or audio transducer(s) 260 and associated recording and analysis systems may be configured to detect and record any one or all of S1, S2, S3, and S4. Other heart sound parameters which may be monitored and recorded by the heart sound recording and monitoring system may include any one or more of electromechanical activation time (EMAT), percentage of EMAT (% EMAT), systolic dysfunction index (SDI), and left ventricular systolic time (LVST). EMAT is generally measured from the onset of the Qwave on the ECG to the closure of the mitral valve within the S1 heart sound. Prolonged EMAT has been associated with reduced left ventricular ejection fraction (LV EF, being a measure of how much blood is being pumped out of the left ventricle of the heart with each contraction). % EMAT is EMAT divided by the dominant RR interval. % EMAT is related to the efficiency of the pump function of the heart. SDI is a multiplicative combination of ECG and sound parameters (EMA, S3, QRS duration and QR interval). SDI predicts left ventricular systolic dysfunction with high specificity. LVST is defined as the time interval between the S1 and the S2 heart sounds. It is the systolic portion of the cardiac cycle. LVST has some heart rate dependence, and tends to be approximately 40% (range 30-50%) of the cardiac cycle but is affected by disease that produces poor contractility and/or a low ejection fraction.

Data regarding any one or more of the above referenced heart sound parameters may be recorded and displayed in, for example, trend charts that may be accessed by a subject or care provider through the control unit 120 or an external device. Additionally, control limits regarding any one or more of these heart sound parameters may be set. The control unit 120 or an external system to which the heart sound data is transmitted may compare the observed (or calculated) heart sound parameters with the control limits and if any one or more of the control limits are violated a warning may be provided to the subject, for example, through a speaker or display of the control unit 120 or user interface pod 140.

In some embodiments, the acoustic sensor(s) or audio transducer(s) 260 and associated recording and analysis systems may be configured to detect and identify the voice of a subject wearing the wearable medical device so that a patient voice signature may be used as a response mechanism. The processor within the control unit 120 may be trained to recognize the voice of the subject during an initial learning period, using speech recognition and voice analysis methods known in the art. The control unit 120 may then prompt the subject, for example, through a speaker or a display, to indicate whether the subject is conscious by saying a predetermined word or phrase. For example, where the control unit 120 determines that the subject is experiencing cardiac arrhythmia, the control unit 120 may issue an audible alarm via a speaker (not shown) on the control unit 120 and/or the user interface pod 140 alerting the subject and any bystanders to the subject's medical condition. The control unit 120 may also instruct the subject to speak a word or a phrase, which is detected by the acoustic sensor(s) or audio transducer(s) 260 and transmitted to the control unit 120, to indicate that the subject is conscious, thereby instructing the control unit 120 to withhold the delivery of one or more therapeutic defibrillating shocks. If the subject does not respond, the device may presume that the subject is unconscious, and proceed with the treatment sequence, culminating in the delivery of one or more defibrillating shocks to the body of the subject.

The control unit 120 may be configured to differentiate between the voice of the subject and the voice of a person other than the subject, for example, a bystander, first responder, or professional EMT. If, in response to a prompt, a person speaks, the control unit 120 may analyze the voice to determine whether the voice is that of the subject or another. If it is the voice of another, the control unit 120 may repeat its instructions to the subject to speak a word or a phrase. The control unit may modify the instructions to request silence from other persons around the subject so that the subject may comply with the instructions. In addition, if, in response to a prompt, the subject does not respond by speaking, the control unit 120 may monitor a signal from the acoustic sensor(s) or audio transducer(s) 260 to determine if other persons are present proximate the subject. If the control unit 120 detects a voice of a person indicative of the presence of the person proximate the subject, the control unit 120 may issue instructions, for example, through a speaker or a display, requesting the person to take some action, for example, to provide the control unit 120 with information regarding the state of the subject through an interface of the control unit 120, to call for assistance, to indicate when professional assistance has arrived, or perform one or more other actions. The control unit 120 may alter a course of treatment, for example, postpone or abort the delivery of one or more defibrillating shocks to the body of the subject, provide data about the subject and his condition, if, for example, the presence of a bystander is detected by detection of the voice of the bystander, and the bystander responds to a prompt by the control unit 120 indicating that professional assistance has arrived to assist the subject. The control unit 120, upon identification of the presence of professional assistance, may also move into an alternate mode of operation in which the ambulatory medical monitoring and treatment device 100 operates as support for the medical assistance being provided.

As discussed above, to provide protection against cardiac arrest, subjects that use a wearable medical device, such as a wearable defibrillator, generally wear the device nearly continuously while they are awake and while they are asleep. Because the wearable medical device is worn nearly continuously, dry electrodes are typically used for both the plurality of ECG sensing electrodes 112 and the plurality of therapy electrodes 114a, 114b for comfort and to prevent irritation of the subject's skin. Where it is determined that one or more defibrillating shocks are to be delivered to the body of the subject and the subject is non-responsive, the control unit 120 sends a signal to the plurality of therapy electrodes 114a, 114b causing them to release an impedance reducing gel prior to delivery of one or more defibrillating shocks. The impedance reducing gel reduces the impedance between the conductive surface of the therapy electrodes and the subject's skin, thereby improving the efficiency of the energy delivered to the subject and reducing the chance of damage (for example, in the form of burning, reddening, or other types of irritation) to the subject's skin.

Figure 2A:
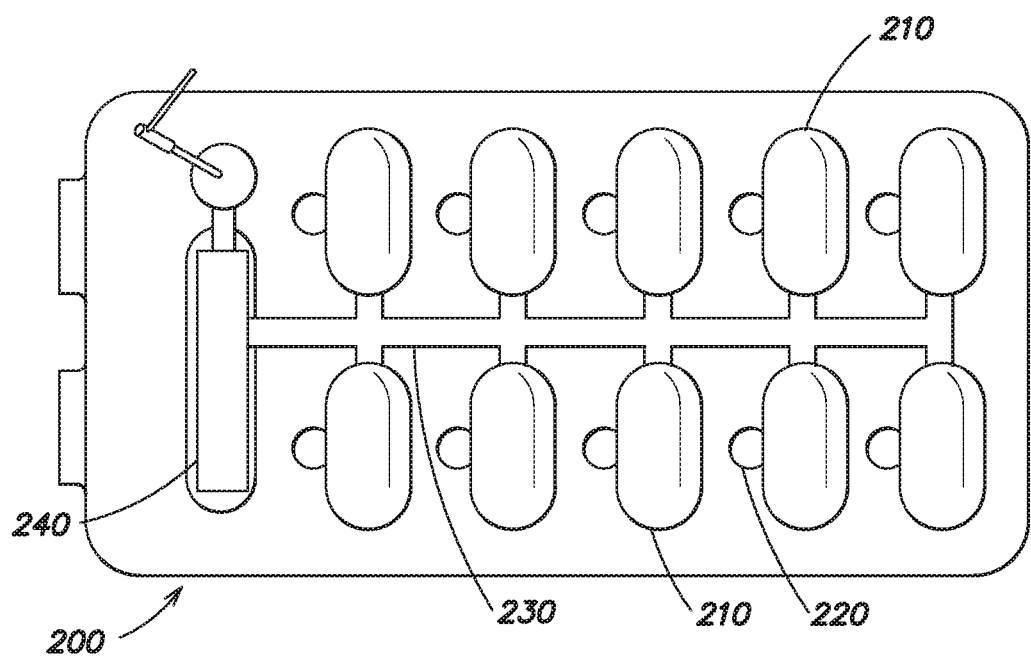
FIG. 2A is a plan view of an electrode portion of a therapy electrode assembly that may be used with the wearable medical device illustrated in FIG. 1.
Figure 2B:
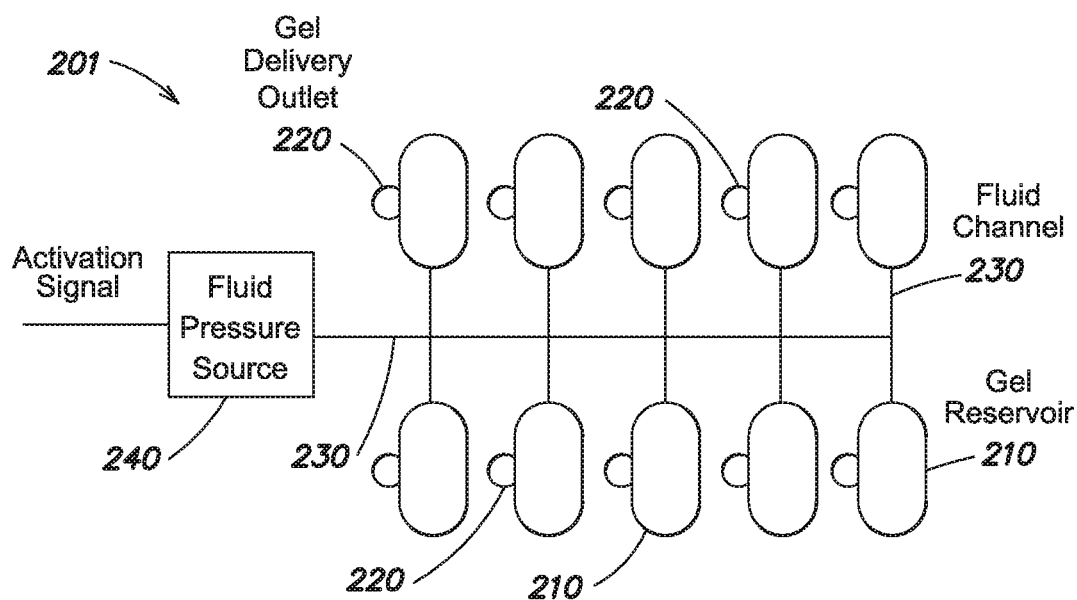
FIG. 2B is a functional block diagram of an impedance reduction system that may be included in the electrode portion of FIG. 2A.

FIG. 2A is a plan view of an electrode portion of a therapy electrode assembly that includes an impedance reduction system and which may be used with a wearable medical device, such as the wearable defibrillator described above with respect to FIG. 1. FIG. 2B is a functional block diagram of the impedance reduction system that is included in the electrode portion of the therapy electrode assembly shown in FIG. 2A. The impedance reduction system, when activated, dispenses an impedance reducing (i.e., electrically conductive) gel onto the exposed surface of the electrode portion of the therapy electrode assembly that, in use, is placed most proximate to the subject's body. The electrode portion 200 is a multiple layer laminated structure that includes an electrically conductive layer 202 (not visible in FIG. 2A, but disposed on the bottom surface of the embodiment of the electrode portion 250 shown in FIG. 2D) that forms the electrode and an impedance reduction system 201. In use, the electrically conductive layer is disposed adjacent the subject's skin, although the conductive layer need not make direct contact with the subject, as portions of the harness 110 (FIG. 1) and/or portions of the subject's clothing may be present between the electrically conductive layer and the subject's skin. As shown in FIG. 2A, the impedance reduction system 201 is disposed on a side of the electrode portion 200 (i.e., the top-side shown in FIG. 2A) that is opposite the side on which the conductive layer is formed.

The impedance reduction system 201 includes a plurality of conductive gel reservoirs 210, each of which has a respective gel delivery outlet 220, that are fluidly coupled to a fluid channel 230, and a fluid pressure source 240. The fluid pressure source 240 is fluidly coupled to the fluid channel 230, and when activated by an activation signal, forces a fluid, such as nitrogen gas, into the channel 230. The hydraulic pressure of the fluid from the activated fluid pressure source 240 in the fluid channel 230 forces the conductive gel stored in each of the plurality of gel reservoirs out of the plurality of gel delivery outlets 220 through apertures formed in the electrically conductive layer and onto the exposed surface of the electrically conductive layer that, in use, is placed most proximate to the subject's body. The apertures in the electrically conductive layer are generally aligned with the plurality of gel delivery outlets 220 so that when activated, the electrically conductive gel is dispensed onto the exposed surface of the electrode portion that is disposed most proximate to the subject's body. Further details regarding the construction of the electrode portion 200 are described in U.S. Pat. No. 5,078,134 (hereinafter "the '134 patent") which is incorporated herein by reference.

Figure 2C:
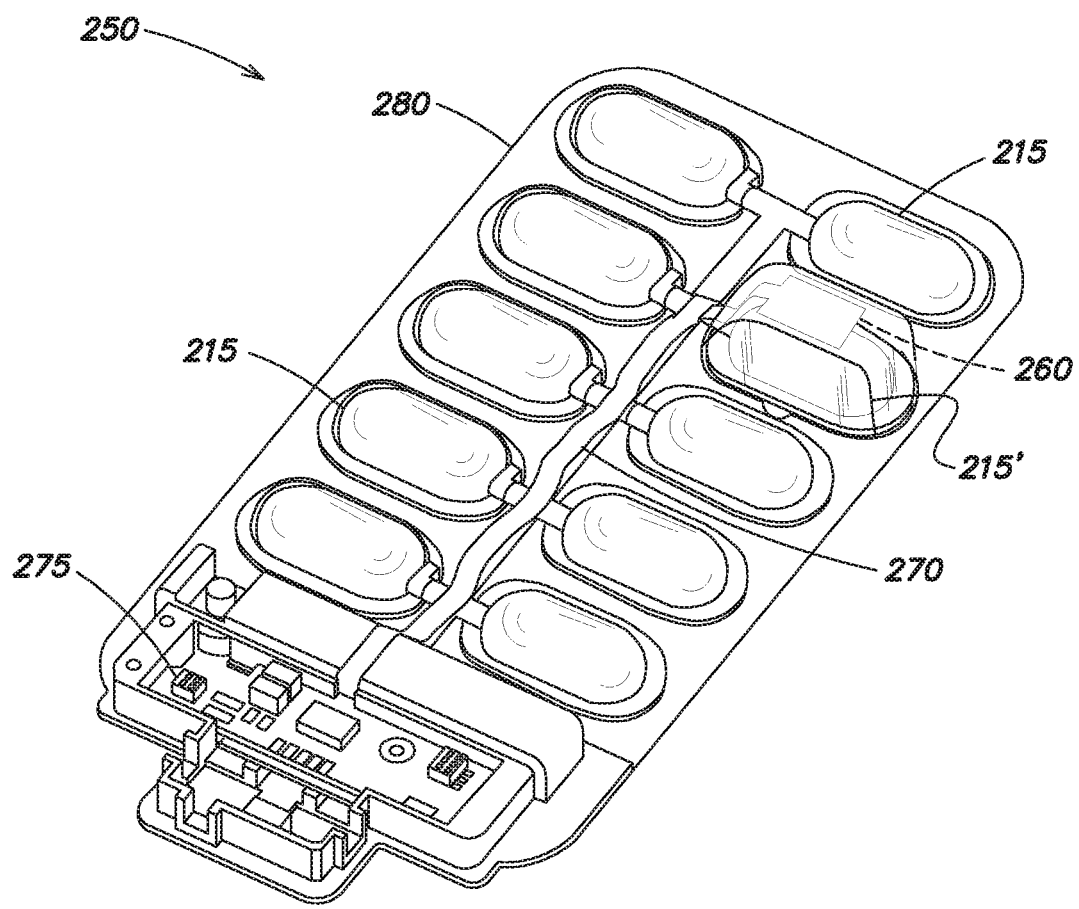
FIG. 2C is an isometric view of another embodiment of an electrode portion of a therapy electrode assembly that may be used with the wearable medical device illustrated in FIG. 1.
Figure 2D:
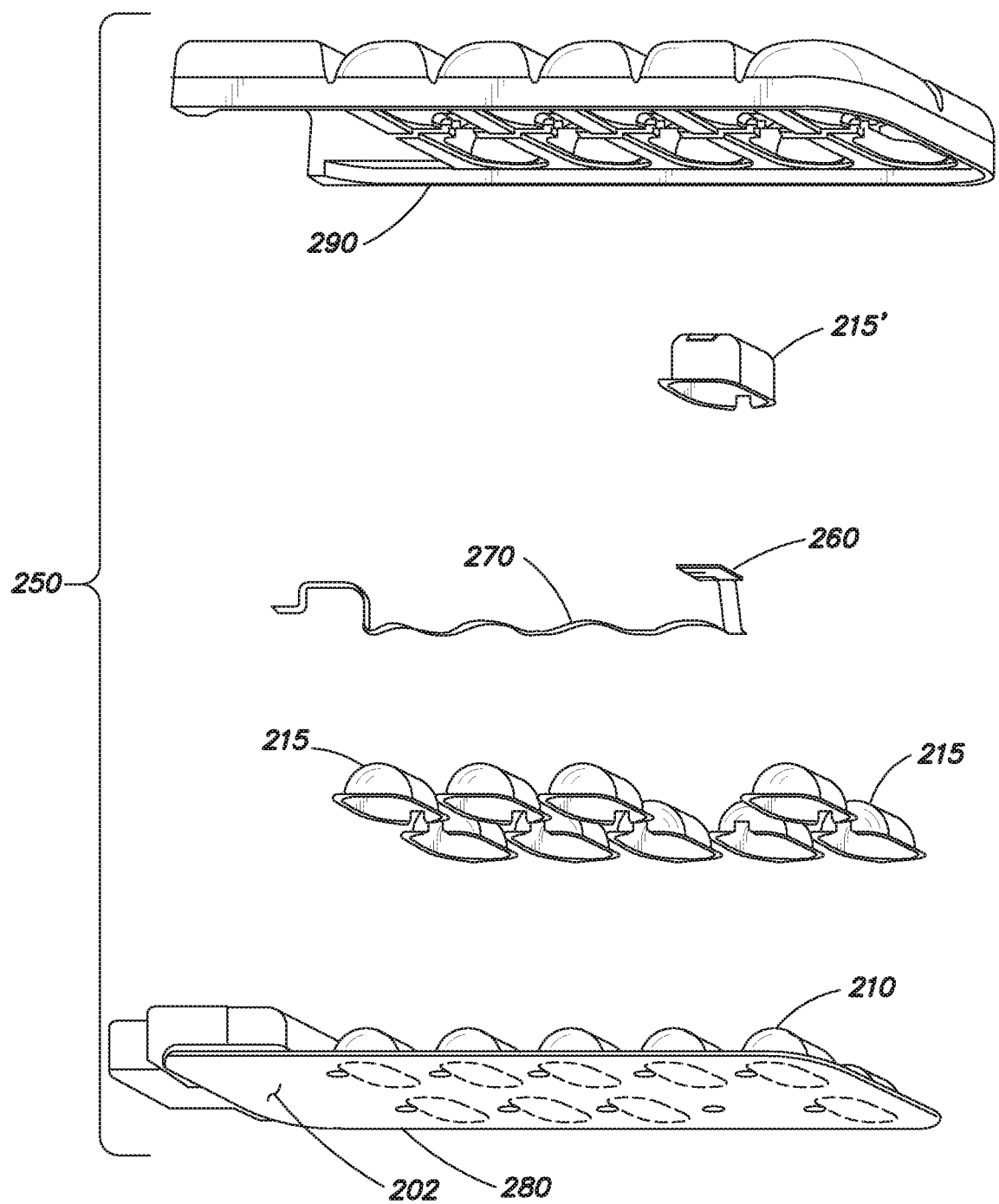
FIG. 2D is an exploded view of the electrode portion of FIG. 2C.

FIG. 2C illustrates an electrode portion 250 of a therapy electrode assembly including an acoustic sensor 260. FIG. 2D is an exploded view of the electrode portion of FIG. 2C. The exposed conductive surface of the electrode portion is dimensioned to be capable of delivering large amounts of energy to a subject, for example, about 200 Joules, such as to perform defibrillation. The acoustic sensor 260 is illustrated in FIG. 2C as disposed within a cap 215' enclosing one of the conductive gel reservoirs 210 of the electrode portion 250. The cap 215' is formed of a sound conducting material, for example, a hard plastic. The cap 215' is illustrated as transparent in FIG. 2C to better illustrate the position of the acoustic sensor 260. The acoustic sensor 260 is mechanically and acoustically coupled to an upper internal wall of the cap 215' with an adhesive, for example, epoxy or another form of glue, or by one or more mechanical fasteners, for example, one or more snaps, tabs, or other fasteners known in the art. A space is provided between the conductive gel reservoir 210 within the shell 215' and the acoustic sensor 260. The acoustic sensor 260 is positioned and arranged to be acoustically coupled to the body of a subject to which the electrode portion 250 is applied. The acoustic coupling of the acoustic sensor 260 to the body of a subject to which the electrode portion 250 is applied may be through the shell 215' and the substrate 280. The acoustic coupling may be facilitated by the minimization or elimination of any gaps between the acoustic sensor 260 and shell 215' and between the shell 215' and the substrate 280 of the electrode portion 250. A protective cover 290 which may be formed from, for example, foam rubber, may be provided to cover the upper face of the electrode portion 250.

The cap 215' housing the acoustic sensor 260 may in some embodiments be shaped differently than caps 215 enclosing the conductive gel reservoirs 210 of the electrode portion 250 which do not include the acoustic sensor 260. For example, the cap 215' including the acoustic sensor may have an upper wall which is flattened to facilitate attachment of the acoustic sensor 260. The caps 215 which do not include acoustic sensors may, in contrast, have substantially rounded upper walls.

A connector or signal conductor 270 which may include, for example, a plurality of wires, a ribbon cable, a coaxial cable, or other forms of electrical signal conductors known in the art provides electrical connection between the acoustic sensor 260 and a circuit board 275 coupled to the electrode portion 250. In some embodiments, the signal conductor is coupled, for example, by an adhesive or one or more mechanical fasteners to one or more portions of the electrode portion 250. As illustrated in FIG. 2C, the signal conductor 270 may be provided with some slack by, for example, being routed along a multi-dimensional path such that it allows for flexure of the electrode portion 250 without becoming detached from the acoustic sensor 260 or circuit board 275. The provision of slack in the signal conductor may be especially desirable in electrode portions 250 which have been designed for enhanced flexibility, for example, one or more of the electrode portions disclosed in co-owned U.S. Pat. No. 8,880,196, titled FLEXIBLE THERAPY ELECTRODE, which is incorporated by reference herein in its entirety.

In other embodiments, the acoustic sensor 260 may be located on or in other areas of the electrode portion 250. For example, as illustrated in FIG. 3B, the acoustic sensor 260 may be disposed on a portion of the flat substrate 280 of the electrode portion 250. The acoustic sensor 260 may in alternate embodiments be disposed in any location where it may acoustically couple to the body of a subject. The electrode portion 250 may include a single acoustic sensor as illustrated, or may include multiple acoustic sensors 260.

The acoustic sensor 260 may comprise any device that may detect sounds from a subject's heart and provide an output signal responsive to the detected heart sounds. In some embodiments the acoustic sensor 260 comprises a microphone. In some embodiments the acoustic sensor 260 comprises an accelerometer. The acoustic sensor 260 may comprise a microelectromechanical system (MEMS) accelerometer. In some embodiments the acoustic sensor 260 comprises a multi-channel accelerometer, for example, a three-channel accelerometer. The acoustic sensor may comprise a three-channel accelerometer configured to sense movement in each of three orthogonal axes. An example of an accelerometer which may be utilized in some embodiments is a LIS344ALH accelerometer, available from STMicroelectronics. The acoustic sensor 260 and associated electronics may be configured to monitor any one or more of a subject's respiration, a subject's heart sounds, a subject's position, and an activity level of a subject. The acoustic sensor 260 and associated electronics may additionally or alternatively be configured to monitor other sounds which may be indicative of a state of health of a subject, for example, gastrointestinal sounds or the sounds of snoring or the absence of such sounds, for example, to provide an indication of the subject experiencing sleep apnea. The acoustic sensor 260 may provide signals indicative of the subject's respiration on a first channel, signals indicative of the subject's heart sounds on a second channel, and signals indicative of the subject's position on a third channel. In other embodiments, the different channels may be utilized to provide signals indicative of more than one physiological parameter or other parameter associated with the state of the subject. For example, in one embodiment, the acoustic sensor 260 may provide signals indicative of the subject's heart sounds on a first channel, signals indicative of the subject's respiration on a second channel, and signals indicative of the subject's body position on any or all of the first, second, and third channel. It should be appreciated that dependent on the underlying parameter that is being monitored, multiple signals related to the parameter being monitored may be received over a single channel or a number of different channels. The acoustic sensor 260 and associated electronics may also in some embodiments be configured to detect sounds associated with the release of conductive gel from the conductive gel reservoirs 210 of an electrode portion 250 of a therapy electrode assembly and provide an indication of the release of the conductive gel to a controller or alarm system associated with the therapy electrode assembly.

Further, when including an accelerometer, the acoustic sensor 260 and associated electronics may be configured to provide an indication of whether a therapy electrode assembly including the acoustic sensor has been correctly placed on a subject. The acoustic sensor 260 and associated electronics may be configured to detect, for example, by sensing the direction of the pull of the Earth's gravity, the orientation of the acoustic sensor 260, and of the therapy electrode assembly in which it is included. The acoustic sensor 260 and associated electronics may thus be utilized to provide an indication of whether the therapy electrode assembly has been correctly placed on a subject or whether it has been incorrectly placed, for example, in an inverted position.

The acoustic sensor 260 and associated electronics may be configured to detect whether CPR is being performed on the subject and to output a signal responsive to the detection of the performance of CPR. Further, electronics associated with the acoustic sensor 260 may be configured to analyze the motion associated with the performance of CPR, for example, the rate and depth of chest compressions. In some embodiments, an acoustic sensor 260 may be provided on a portion of a therapy electrode assembly, for example, a tab extending from an electrode portion 250, or on a position of a wearable medical device 100, which would be proximate the xiphoid 116 of a subject when worn by the subject, as illustrated in FIG. 1. Such placement of an acoustic sensor would facilitate measuring the depth of chest compressions during the administration of CPR to the subject in addition to detecting whether CPR is being performed. The electronics associated with the acoustic sensor 260 may be configured to provide feedback to a person administering the CPR through, for example, one or more indicators or through a speaker to adjust the rate and/or depth of chest compressions to provide for a more effective administration of CPR.

Applicants have appreciated that there may be instances where it would be desirable to have redundancy in the impedance reduction system described above. Electrodes including redundant impedance reduction systems are disclosed in co-owned U.S. Pat. No. 8,406,842 which is incorporated by reference herein in its entirety.

Figure 3A:
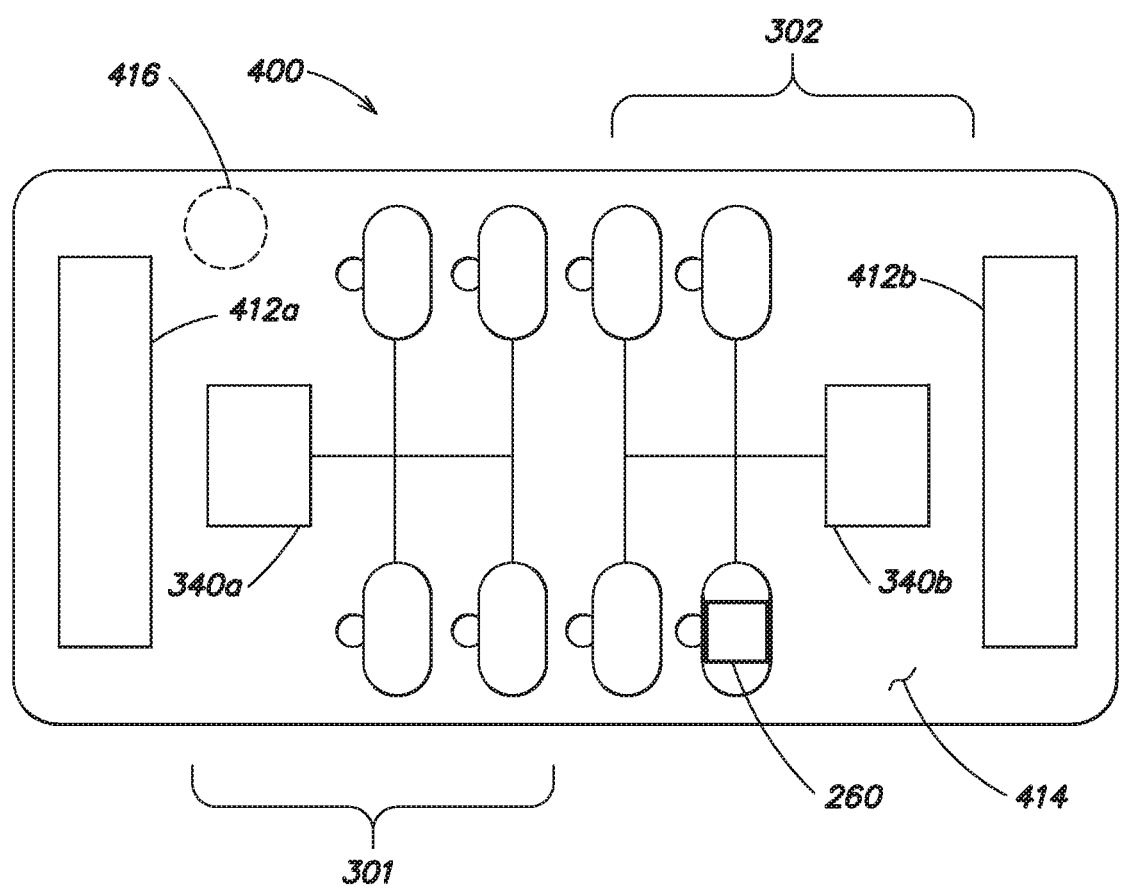
FIG. 3A is a schematic diagram of an electrode assembly that includes ECG sensing electrodes, a therapy electrode, and redundant impedance reduction systems in accordance with another aspect of the present invention.
Figure 3B:
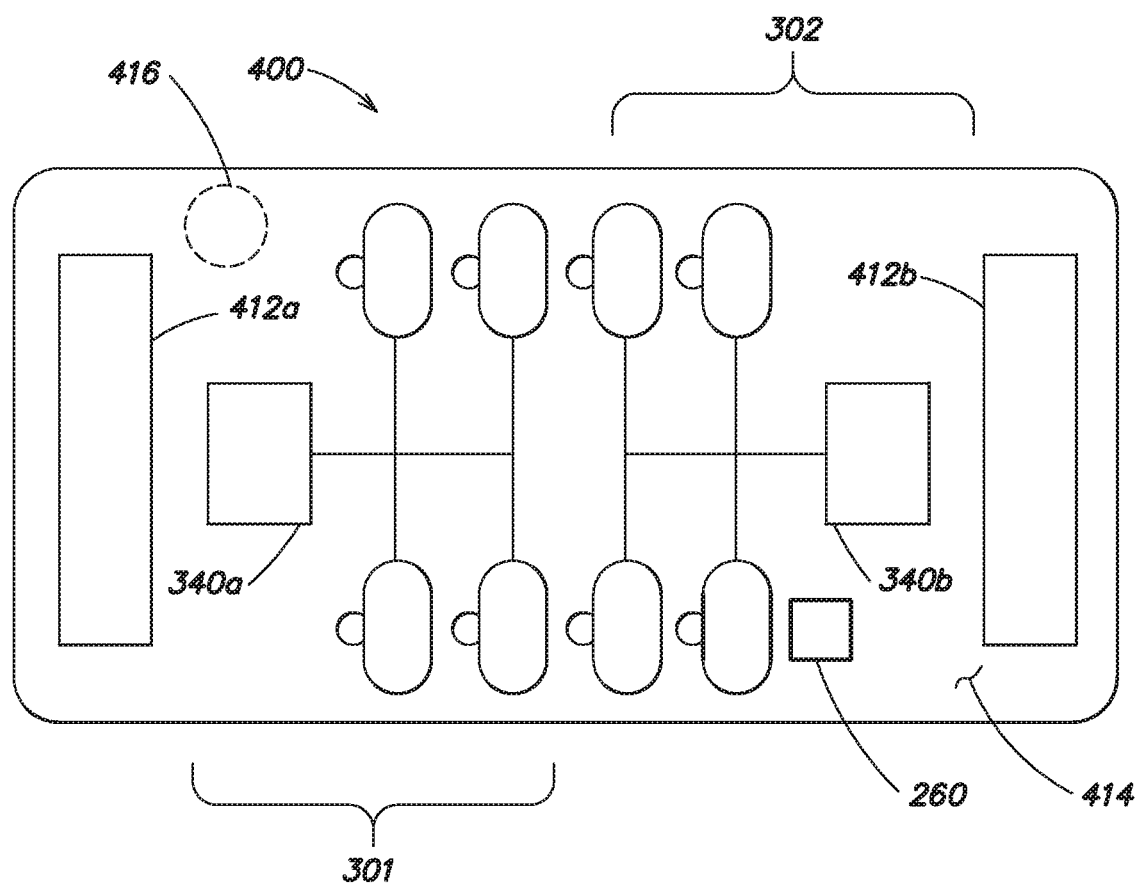
FIG. 3B is a schematic diagram of an electrode assembly that includes ECG sensing electrodes, a therapy electrode, and redundant impedance reduction systems in accordance with another aspect of the present invention.

FIG. 3A illustrates an electrode assembly that combines one or more ECG sensing electrodes, a therapy electrode, and redundant impedance reduction systems in a single integrated electrode assembly in accordance with a further aspect of the present invention. As shown, the electrode assembly 400 includes a pair of ECG sensing electrodes 412*a*, 412*b* for monitoring the cardiac function of a subject. The electrode assembly 400 further includes a therapy electrode 414, and at least two impedance reduction systems 301, 302. The pair of ECG sensing electrodes 412*a*, 412*b* may be electrically separated from the therapy electrode 414, for example, by an insulator. It should be appreciated that in other embodiments, the electrode assembly 400 may include only a single ECG sensing electrode, while in other embodiments, more than two ECG sensing electrodes may be provided. In such alternative embodiments, the number and placement of ECG sensing electrodes may vary from that shown in FIG. 3A. In yet a further embodiment, the integrated electrode assembly may include additional sensors 416, other than the one or more ECG sensing electrodes and the therapy electrode, that are capable of monitoring other physiological parameters of a subject, such as blood pressure, heart rate, thoracic impedance, pulse oxygen level, respiration rate, heart sounds, etc. The additional sensors 416 may include, for example, one or more acoustic sensors 260.

Figure 4:
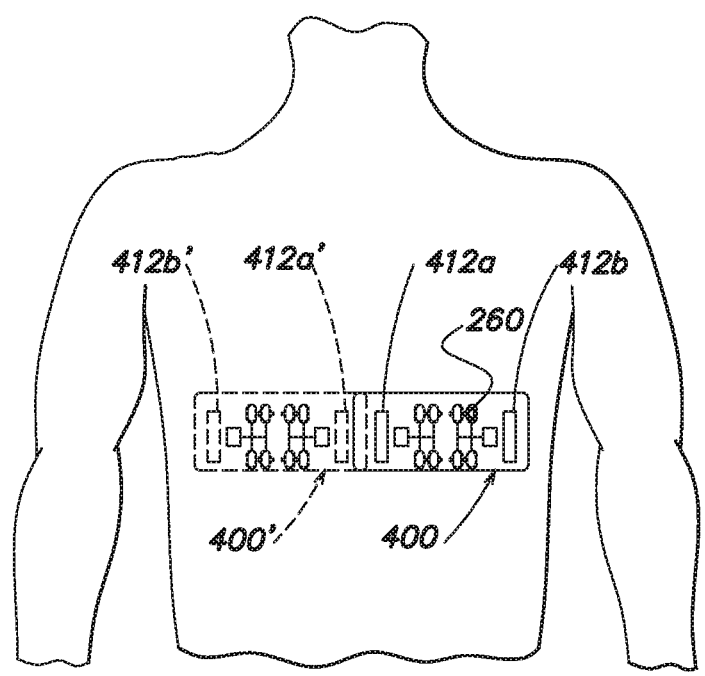
FIG. 4 illustrates the manner in which the electrode assembly of FIG. 3A may be worn on the body of a subject.

The electrode assembly 400 may be worn on the subject's body such that one of the pair of ECG sensing electrodes 412a, 412b is disposed approximately in the center of the subject's torso, and the other of the pair of ECG sensing electrodes 412a, 412b is disposed on the side of the subject's torso. For example, as shown in FIG. 4, the electrode assembly 400 may be worn on the front of the subject's torso, so that the ECG sensing electrode 412a is disposed approximately in the center of the subject's chest, and the other ECG sensing electrode 412b is disposed on the subject's side. A second electrode assembly 400' may be worn on the back of the subject's torso to provide a second pair of ECG sensing electrodes 412a', 412b', so that one of the ECG sensing electrodes (for example, ECG sensing electrode 412a') of the second pair of ECG sensing electrodes 400' is disposed approximately in the center of the subject's back, and the other ECG sensing electrode (for example, ECG sensing electrode 412b') of the second pair of ECG sensing electrodes 400' is disposed on the subject's side opposite the other ECG sensing electrode (for example, ECG sensing electrode 412b) of the first pair of ECG sensing electrodes 412a, 412b, as shown in FIG. 4. Such an arrangement provides a front-to-back pairing of ECG sensing electrodes (for example, 412a, 412a') and a side-to-side pairing of ECG sensing electrodes (for example, 412b, 412b'). It should be appreciated that other placements for the first electrode assembly 400 and the second electrode assembly 400' may alternatively be used. For example, the first electrode assembly 400 may be placed on one side of the subject's torso, and the second electrode assembly 400' placed on the other side of the subject's torso to provide side-to-side pairings of ECG sensing electrodes.

The first and second electrode assemblies 400, 400' may include an electrically conductive adhesive layer so that the electrodes assemblies may be directly attached to the subject's skin, or alternatively, they may be attached to the harness as depicted in FIG. 1 and held in position against the torso of the subject. Where only one of the electrode assemblies includes an acoustic sensor 260, the electrode assembly may be positioned so that the acoustic sensor is disposed proximate the subject's heart.

In further embodiments, acoustic sensors 260 for monitoring any of the various parameters described herein, for example, sounds associated with a subject's heart or respiration, orientation of a subject, or motion associated with the administration of CPR to a subject, etc., may be included in electrodes having shapes and materials of construction different from those depicted in, for example, FIGS. 2C and 2D. For example, acoustic sensors may be included in electrodes which consist essentially of a conductive layer and a conductive adhesive or adhesive film for retaining the electrode on the skin of a subject. Electrodes which may include acoustic sensors 260 having the functionality described herein are not limited to any particular form or type.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A therapeutic device comprising:
   an ECG sensing electrode configured to be disposed on a torso of a subject;
   a therapy electrode to be disposed on the torso of the subject, the therapy electrode comprising a substrate and a conductive layer disposed on a lower surface of the substrate; and
   an acoustic sensor coupled to one of the ECG sensing electrode and the therapy electrode, the acoustic sensor being configured to acoustically couple to the torso of the subject and monitor heart sounds indicative of a state of health of a heart of the subject,
   the therapeutic device being configured to store data regarding the heart sounds monitored by the acoustic sensor and transmit the stored data to an external system for processing and analysis.

2. The therapeutic device of claim 1, wherein the acoustic sensor is a MEMS accelerometer.

3. The therapeutic device of claim 2, wherein the acoustic sensor is a multi-axis, multiple-channel MEMS accelerometer.

4. The therapeutic device of claim 1, wherein the therapy electrode and the ECG electrode are included in a multi-function electrode.

5. The therapeutic device of claim 1, wherein the therapy electrode further comprises an electrically conductive gel reservoir configured to release an electrically conductive gel onto a surface of the conductive layer of the therapy electrode, and the acoustic sensor is disposed on a housing of the conductive gel reservoir.

6. The therapeutic device of claim 1, wherein the acoustic sensor is disposed on the substrate of the therapy electrode.

7. The therapeutic device of claim 1, further comprising a control unit configured to monitor a medical condition of the subject and deliver a defibrillation shock to the subject via the therapy electrode responsive to detecting cardiac arrhythmia in the subject.

8. A therapeutic device comprising:
   a therapy electrode configured to deliver electrical therapy to a subject; and
   an acoustic sensor mechanically coupled to the therapy electrode and configured to acoustically couple to a body of the subject to which the therapy electrode is applied and to detect sounds indicative of a state of health of the subject,
   the therapeutic device configured to transmit data regarding the sounds detected by the acoustic sensor to an external system for processing and analysis.

9. The therapeutic device of claim 8, configured to wirelessly transmit the data regarding the sounds detected by the acoustic sensor to the external system.

10. The therapeutic device of claim 8, wherein the acoustic sensor is configured to detect heart sounds of the subject.

11. The therapeutic device of claim 8, wherein the acoustic sensor is a MEMS accelerometer.

12. The therapeutic device of claim 11, wherein the acoustic sensor is a multi-axis, multiple-channel MEMS accelerometer.

13. The therapeutic device of claim 12, wherein the acoustic sensor and associated electronics are configured to provide an indication of whether the therapeutic device has been correctly oriented on the subject.

14. The therapeutic device of claim 12, wherein the therapy electrode is included in a multi-function electrode, the multi-function electrode further configured to monitor an ECG of the subject.

15. The therapeutic device of claim 8, further comprising a control unit configured to monitor a medical condition of the subject and deliver a defibrillation shock to the subject via the therapy electrode responsive to detecting cardiac arrhythmia in the subject.

16. A wearable medical device comprising:
a plurality of therapy electrodes configured to deliver electrical therapy to a subject; and
an acoustic sensor mechanically coupled to at least one of the plurality of therapy electrodes and configured to acoustically couple to a body of the subject wearing the wearable medical device and to monitor heart sounds indicative of a state of health of a heart of the subject, the wearable medical device being configured to store data regarding the heart sounds monitored by the acoustic sensor and transmit the stored data to an external system for processing and analysis.

17. The wearable medical device of claim 16, further comprising one or more additional acoustic sensors disposed on or within one or more portions of the wearable medical device.

18. The wearable medical device of claim 17, further comprising an ECG electrode, wherein the one or more additional acoustic sensors are coupled to the ECG electrode.

19. The wearable medical device of claim 17, wherein the one or more additional acoustic sensors are disposed within at least one other of the plurality of therapy electrodes.

20. The wearable medical device of claim 16, wherein one of the acoustic sensor or the one or more additional acoustic sensors are disposed proximate to or in contact with skin of the subject proximate the subject's heart when the wearable medical device is worn by the subject.

* * * * *